US010786514B2

(12) United States Patent
Mallard et al.

(10) Patent No.: US 10,786,514 B2
(45) Date of Patent: Sep. 29, 2020

(54) DOSAGE REGIMENT OF FERRIC MALTOL (71) Applicant: Shield TX (UK) Limited, Gateshead Quays (GB)

(72) Inventors: Nicholas Mallard, Gateshead Quays (GB); Carl Andrew Sterritt, Gateshead Quays (GB); Julian David Howell, Gateshead Quays (GB)

(73) Assignee: Shield TX (UK) Limited, Gateshead Quays (GB)

( * ) Notice: Subject to any disclaimer, the term of this patent is extended or adjusted under 35 U.S.C. 154(b) by 0 days.

(21) Appl. No.: 15/520,753

(22) PCT Filed: Oct. 21, 2015

(86) PCT No.: PCT/IB2015/058115
§ 371 (c)(1),
(2) Date: Apr. 20, 2017

(87) PCT Pub. No.: WO2016/063228
PCT Pub. Date: Apr. 28, 2016

(65) Prior Publication Data
US 2017/0304314 A1    Oct. 26, 2017

(30) Foreign Application Priority Data
Oct. 21, 2015 (GB) .................... 1418710.8

(51) Int. Cl.
A61K 31/555 (2006.01)
A61K 9/00 (2006.01)

(52) U.S. Cl.
CPC .......... *A61K 31/555* (2013.01); *A61K 9/0053* (2013.01)

(58) Field of Classification Search
CPC ........................... A61K 31/555; A61K 9/0053
See application file for complete search history.

(56) References Cited

U.S. PATENT DOCUMENTS

| 6,339,080 | B1* | 1/2002 | Stockham | A61K 31/295 |
| | | | | 424/DIG. 15 |
| 2008/0234226 | A1 | 9/2008 | Erichsen et al. | |
| 2012/0288530 | A1* | 11/2012 | Bordoloi | A61L 24/106 |
| | | | | 424/400 |
| 2014/0088064 | A1 | 3/2014 | Stockham | |
| 2016/0324822 | A1 | 11/2016 | Schweiger et al. | |

FOREIGN PATENT DOCUMENTS

| JP | S58-159421 A | 9/1983 |
| JP | 2000-229860 A | 8/2000 |
| JP | 2001-505928 A | 5/2001 |
| JP | 2006-063086 A | 3/2006 |
| JP | 2007-505146 A | 3/2007 |
| JP | 2008-539729 A | 11/2008 |
| JP | 2009-515909 A | 4/2009 |
| JP | 2013-032308 A | 2/2013 |
| WO | 2002024196 A1 | 3/2002 |
| WO | 2009138761 A1 | 11/2009 |
| WO | 2012/101442 A1 | 8/2012 |
| WO | 2015101971 A1 | 7/2015 |

OTHER PUBLICATIONS

Harvey et al, Aliment Pharmacol Ther 1998, 12, 845-848.*
And Babitt et al, J Am Soc Nephrol. Sep. 28, 2012; 23(10): 1631-1634.*
Kelsey et al, Journal of Clinical Pharmacy and Therapeutics (1991) 16, 117-122.*
Johnson-Wimbley, Therap Adv Gastroenterol. May 2011; 4(3): 177-184. (Year: 2011).*
Bergamaschi et al., "Prevalence and pathogenesis of anemia in inflammatory bowel disease. Influence of anti-tumor necrosis factor-a treatment" Haematologica 95(2):199-205, 2010.
Brise et al., "Absorbability of different iron compounds" ACTA Med. Scand. 171 (Suppl. 376):23-37, 1962.
British National Formulary, Nutrition and Blood. BMJ Publishing Group and RPS Publishing, London 51:463-4, 2006.
Dudkowiak et al., "Hepcidin and its Role in Inflammatory Bowel Disease" Adv. Clin. Exp. Med. 22(4):585-591, 2013.
Gasche et al., "DOP079, Correcting iron deficiency anaemia in IBD: A pivotal phase 3 study of a novel oral ferric iron" XP002738114, retrieved from internet: Apr. 1, 2015.
Harvey et al., "Ferric trimaltol corrects iron deficiency anaemia in patients intolerant of iron" Aliment Pharmacol. Ther. 12:845-848, 1998.
International Search Report and Written Opinion, PCT/IB2015/058115, dated Jan. 12, 2016.
Kawai et al., "A case of ulcerative colitis induced by oral ferrous sulphate" ACTA Paediatr. Jpn. 34(4):476-8, Aug. 1992.
Kelsey et al., "Absorption of low and therapeutic doses of ferric maltol, a novel ferric iron compound, in iron deficient subjects using a single dose iron absorption test" J. of Clin. Pharm & Ther. 16:117-122, 1991.
Kerr, D., "Gastrointestinal tolerance to oral iron preparation" Lancet ii:489-92, 1958.
Makrides et al., "Efficacy and tolerability of low-dose iron supplements during pregnancy: a randomized controlled trial" Am. J. of Clin. Nutrition 78:145-53, 2003.
Reffitt et al., "Assessment of iron absorption from ferric trimaltol" Annals of Clin. Biochem., British Medical Assoc., London 37(4):457-466, Jan. 1, 2000.
Rimon et al., "Are we giving too much iron? Low-dose iron therapy is effective in octogenarians" Am. J. of Med. 118:1142-1147, 2005.
Slivka et al., "Hydroxyl radicals and toxicity of oral iron" Biochem Biopharmacol. 35:553-6, 1986.
UKIPO Search Report for GB Application No. 1418710.8, dated Jun. 30, 2015.

(Continued)

*Primary Examiner* — Jean P Cornet
(74) *Attorney, Agent, or Firm* — McCarter & English, LLP; Steven G. Davis; Mei Bai (57) ABSTRACT

The present invention relates to a dosage regimen of ST10 (ferric maltol) for use in the treatment of patients suffering from iron deficiency with or without anaemia. The invention specifically relates to use of ST10 wherein the dose is between 40 mg and 90 mg twice daily.

25 Claims, 6 Drawing Sheets

(56) References Cited

OTHER PUBLICATIONS

Wilson et al., "Prevalence and outcomes of anaemia in inflammatory bowel disease" Am. J. Med 116(7A):44S-49S, 2004.
Anonymous, Ferric trimaltol: Phase III data. BioCentury Week in Review, 1 page, Jan. 13, 2014.
Anonymous, Oral ferric iron for iron deficiency anaemia in ulcerative colitis. EFCCA, 1 page. (2011).
United Kingdom Search Report for Application No. GB1400171.3, dated Jul. 4, 2014. 4 pages.
International Search Report and Written Opinion for Application No. PCT/IB2015/050098 dated Jun. 10, 2015.
U.S. Appl. No. 15/110,003, filed Jul. 6, 2016, 2016-0324822.
Fairbanks et al., Iron Deficiency. Williams Hematology, Sixth Edition. McGraw-Hill Medical Publishing Division, New York, Ernest Beutler (Ed.). Chapter 38, pp. 447-470, (2001).

\* cited by examiner

Mean serum concentration-time curves of total Iron after administration of ST10 at 30 mg bid, 60 mg bid and 90 mg bid on day 1

Figure 1

Mean serum concentration-time curves of total iron after administration of ST10 at 30 mg bid, 60 mg bid and 90 mg bid on Day 8

Figure 2

Mean serum value-time curves of transferrin saturation after administration of ST10 at 30 mg bid, 60 mg bid and 90 mg bid on Day 1

Figure 3

Mean serum value-time curves of transferrin saturation after administration of ST10 at 30 mg bid, 60 mg bid and 90 mg bid on Day 8

Figure 4

Mean serum concentration-time curves of soluble transferrin receptor after administration of ST10 at 30 mg bid, 60 mg bid and 90 mg bid on Day 1

Figure 5

Mean serum concentration-time curves of ferritin – change from baseline.

Figure 6

DOSAGE REGIMENT OF FERRIC MALTOL

RELATED APPLICATION INFORMATION

This application is a 35 U.S.C. § 371 national stage filing of International Application No. PCT/IB2015/058115, filed Oct. 21, 2015, which claims priority to United Kingdom Patent Application No. 1418710.8, filed Oct. 21, 2014. The entire contents of each of the foregoing applications are incorporated herein by reference.

The present invention relates to a dosage regimen of ST10 (ferric maltol) for use in the treatment of patients suffering from iron deficiency with or without anaemia. The invention specifically relates to the use of ST10 wherein the dose is between 40 mg and 90 mg twice daily.

BACKGROUND TO THE INVENTION

Iron deficiency is very common and can occur through lack of sufficient iron in the diet, insufficient absorption of iron or from internal bleeding due to diseases of the gastrointestinal tract for example inflammatory bowel diseases (IBD) such as Crohn's disease and ulcerative colitis; and genitourinary diseases such as chronic kidney disease. IBD is a chronic inflammatory disease affecting the gastrointestinal tract and anaemia is recognised as a common and serious complication of IBD. When iron deficiency remains untreated it can lead to iron deficiency anaemia, which is characterised by low levels of iron in the blood and inadequate red blood cells or haemoglobin.

Iron deficiency anaemia (IDA) in inflammatory bowel disease (IBD) is primarily caused by chronic blood loss from inflamed mucosa and/or iron malabsorption in both active and inactive stages of the disease (1). Dietary restriction and highly selective diets amongst IBD patients often result in poor dietary intake, whilst mucosal inflammation in the gastrointestinal tract and systemic inflammation may lead to inadequate nutrient absorption (2). More specifically the production of cytokines in states of chronic inflammation, such as IL-10, lipopolysaccharide, TNF-alpha and hepcidin act via multiple mechanisms to increase the uptake and storage of iron in the reticuloendothelial system, and reduce the uptake of iron from the gut (3). There is a belief that oral iron treatments are particularly poorly tolerated by patients with IBD and reports of oral iron exacerbating IBD disease activity (4). Characteristic symptoms of IDA in IBD include chronic fatigue, headache and impairment of cognitive function.

Iron deficiency, without anaemia, has also been shown to have clinical consequences for patients and individuals. Iron is an important component of many intracellular processes and the effect of iron deficiency or iron deficiency correction has been reported in chronic heart failure, growth, behaviour and learning in children and cognition in the elderly.

Typically, treatment for iron deficiency (with or without anaemia) is in the form of ferrous iron ($Fe^{2+}$) salts, e.g. ferrous sulphate, dosed orally as 200 mg tablets (65 mg elemental iron) three to four times daily. However it is widely accepted that as the duodenum can maximally absorb only 10-15 mg of iron a day, greater than 90% of ingested iron is not absorbed, leading to symptomatic adverse events including toxicity at the gastrointestinal mucosa, abdominal pain, nausea, vomiting, constipation, diarrhoea and dark stools, all of which are dose related and lead to poor adherence with treatment. While the recommended daily dose of elemental iron for treatment of patients with iron deficiency anaemia is stated, for example in the British National Formulary (5), as being between 100-200 mg, recent studies conducted on patients without IBD question the need for such high doses and suggest that little as 15-30 mg elemental iron daily may be adequate (6, 7). This is reported as reasonable since the daily uptake is limited to 10-15 mg and the non-absorbed iron passes areas of intestinal inflammation.

In addition, if ferrous iron tablets become lodged in the upper gastrointestinal tract, contact irritation may occur causing erosion or ulceration. Hence treatment with ferrous iron is badly tolerated leading to poor compliance and significantly reduced therapeutic effect, particularly in patients suffering from IBD who already have significant damage to their gastrointestinal tract (8-9). In fact, treatment with ferrous iron preparations in such patients can often worsen their condition and in some regulatory regions ferrous iron salts are contraindicated for use in IBD patients. In situations where oral ferrous preparations are poorly tolerated or therapeutically ineffective the treatment of choice is currently intravenous iron administration. Because of the gastrointestinal side effects of ferrous iron salts they are recommended to be taken in divided daily doses (e.g. twice or three times a day) and with food; which reduces the incidence of side effects. However the presence of foodstuffs also promotes the formation of insoluble chelates with the ferrous iron, and reduces the functional bioavailability of the oral iron.

Alternative treatment with oral ferric iron ($Fe^{3+}$) salts also results in poor iron absorption due to the ready formation of insoluble chelates when passing from the acidic environment of the stomach to less acidic the small intestine.

ST10, also referred to as ferric trimaltol and ferric maltol, a chemically stable complex formed between ferric iron ($Fe^{3+}$) and maltol (3-hydroxy-2-methyl-4-pyrone) was developed as an alternative to oral ferrous products and has been shown to effectively correct iron deficiency in subjects with a history of ferrous sulphate intolerance (10). ST10 makes iron available in the gastrointestinal tract, providing iron in a biologically labile form for uptake via enterocytes across the intestinal wall (10). Since the iron is stabilized in a chelated form it is less toxic, and this lack of gastrointestinal toxicity means that it can be given on an empty stomach, which improves its functional bioavailability compared to ferrous salts.

Therefore together with its higher functional bioavailability, lower doses of elemental iron are administered, compared to available, approved ferrous forms, thereby improving toxicity, patient compliance and ultimately improved correction of ID.

Previous studies (11) have reported that the most appropriate daily amount of iron delivered as ST10 is 30 mg given twice daily, this dose was based on studies showing that this is the maximal amount of elemental iron that can be absorbed by the gastrointestinal tract and given as a divided dose to maximise tolerability.

Kelsey et al (12) reported single doses of 10 mg and 60 mg of ferric maltol, the 60 mg dose administered as two 30 mg tablets. Although the results were encouraging in comparison to equivalent doses of ferrous sulphate preparations, the pharmacokinetic study did not report on repeated dosing, dosing more than once a day, safety of side effects or efficacy of such a dose, or comment on higher doses of ferric maltol. In addition the absorption of iron from ferric maltol was reported in subjects without active or chronic inflammatory disease.

Harvey et al (13) reported single doses of 30 mg ST10 twice daily in patients recruited from gastroenterology clinics, however those presenting with active inflammatory disease were excluded from the study.

Due to the above described poor profile of oral ferrous compounds and the inherent risk of treatment with intravenous iron there is a continuing need to develop safe and effective methods of delivering iron to subjects in need thereof. In particular there is a need to develop new dosages of ST10 that are efficacious, safe and clinically effective in reducing iron deficiency in patients suffering from iron deficiency with or without anaemia and that are also suitable for treating patients having iron deficiency associated with active or chronic inflammatory disease.

The examples herein demonstrate that higher doses of iron can in fact be tolerated for example in patients with existing IBD, and result in a higher absorption of iron into the blood and into red blood cells, compared to earlier reports. These studies are the first to report efficacious higher doses of iron and provide for new and improved dosage forms for the treatment of iron deficiency and iron deficiency anaemia, as well as maintenance of iron stores in subjects with chronic iron loss or inadequate supply. In addition the examples show that doses of 60-90 mg twice daily are well tolerated, result in greater iron uptake and greater incorporation of iron into haemoglobin forming cells, all in the presence of active IBD; compared to the existing dose of 30 mg twice a day. This is an important finding that would result in improved patient compliance with treatment and better patient outcomes of anaemia and iron deficiency correction. In addition any excess iron was excreted with no adverse side effects confirming that doses can be administered above the previously anticipated maximal level without significant toxicity.

This represents an important development in the treatment of iron deficiency since it is well known that alternative iron treatments, for example ferrous sulphate can be fatal if taken as an accidental overdose, particularly in children. Therefore, the invention provides for an iron composition in the form of ferric maltol that may be safely administered in an amount above the current recommended level, for which there is an unmet medical need.

Dose ranges claimed are safe in the event of overdose since excess iron was excreted at the 90 mg dose. This provides an advantage over existing treatments since ferrous iron treatments are toxic and overdose can be fatal. Therefore, the inventors have surprisingly found that, despite contradictory teachings in the prior art that doses above 30 mg per day would not be beneficial (5-7), dosages of up to 90 mg twice daily result in increased iron absorption and haemoglobin production, appear well tolerated and are in fact safe.

SUMMARY OF THE INVENTION

According to a first aspect of the invention there is provided ST10 for use in the treatment or prevention of iron deficiency with or without anaemia wherein ST10 is administered orally as a 40 mg to 90 mg dose twice daily.

According to a further aspect of the invention there is provided a method of treating a subject suffering from iron deficiency with or without anaemia the method comprising administering orally to the patient a 40 mg to 90 mg ST10 dose twice daily.

DETAILED DESCRIPTION OF THE INVENTION

According to a first aspect of the invention there is provided ST10 for use in the treatment or prevention of iron deficiency with or without anaemia wherein ST10 is administered orally as a 40 mg to 90 mg dose twice daily.

ST10 is also known as ferric trimaltol and ferric maltol is a chemically stable complex formed between ferric iron ($Fe^{3+}$) and maltol (3-hydroxy-2-methyl-4-pyrone) according to the chemical structure below.

The molar ratio of iron to hydroxypyrone is 1:3

Maltol is a naturally occurring sugar derivative and is used in the food industry as a flavour enhancer.

ST10 may be administered orally to a subject as a 40 mg to 90 mg dose, wherein 40 to 90 mg refers to the amount of elemental iron in the dose. The amount of ST10 equivalent to 60 mg of elemental iron ($Fe^{3+}$) is 463.0 mg. The amount of ST10 equivalent to 90 mg of elemental iron ($Fe^{3+}$) is 695.0 mg iron. For the avoidance of doubt, reference to 60 mg ST10 for example, refers to a dose of 463.0 mg of ST10.

In one embodiment the ST10 dose is administered as a 30 mg ST10 preparation comprising 231.5 mg ST10. A 60 mg dose is administered as two 30 mg ST10 preparations taken sequentially at a single time point. Alternatively a 60 mg ST10 dose may be administered as a single 60 mg tablet. A 90 mg dose may be administered as three 30 mg preparations taken sequentially at a single time point.

ST10 may be administered at a dose below 60 mg but above 30 mg, for example as a 35 mg, 40 mg, 45 mg, 50 mg or 55 mg dose. In this case the amounts of ST10 will vary such that the elemental iron is according to the stated dose.

ST10 may be administered as a 60 mg, 65 mg, 70 mg, 75 mg, 80 mg, 85 mg or 90 mg dose. It will be understood that ST10 dose preparations which are not divisible by 30 may be prepared by the skilled person using routine methods known in the art and including known excipients used in oral formulations. For example a 45 mg ST10 preparation will comprise 347.25 mg of ST10. A 55 mg ST10 preparation will comprise 424.4 mg of ST10 in addition to excipients.

In one embodiment the ST10 dose is 60 mg to 90 mg.

In another embodiment the ST10 dose is 65 mg to 90 mg.

In another embodiment the ST10 dose is 60 mg. In further embodiment the ST10 dose is 90 mg.

The subject is a mammal, preferably a human.

It is understood that where a parameter range is provided, all integers within that range, and tenths thereof are also included in the invention. For example 60 mg to 90 mg includes 60.1 mg, 60.2 mg, 60.3 mg and so on up to 90.0 mg.

The ST10 dose is administered twice daily as an oral preparation, for example as a tablet or capsule formulation. Alternatively the ST10 dose is administered once daily, for example when ST10 is in the range 65 mg to 90 mg.

In one embodiment the ST10 dose is administered on an empty stomach. In contrast to ferrous iron treatments, which are required to be taken with food to try to reduce gastrointestinal symptoms, ST10 is taken on an empty stomach to avoid the formation of precipitates with food elements. This offers an advantage over ferrous treatment since it allows for lower dosage of elemental iron and consequently improved tolerability and therefore provides a significant improvement in reduction of side effects and patient compliance.

The ST10 dose may be administered at any time of the day, for example on two separate occasions during the waking hours. In one example the ST10 dose is administered once before breakfast and once prior to sleep. Administration at these times of the day is known to improve patient compliance and reduces the risk of side effects attributed to excess iron. Alternatively the ST10 dose may be administered on two separate occasions during the waking hours when the stomach is empty.

ST10 may be administered once daily as a 90 mg preparation. The inventors have found that 90 mg once or twice daily represents the maximal dose since greater absorption of iron was not observed at this dose. Therefore a plateau of dose response is present between 60 mg and 90 mg twice daily and excess iron that is not absorbed is excreted. In some cases it may be preferable to administer a high ST10 dose, for example 90 mg once or twice daily particularly in patients who have severe iron deficiency and require a high absorption rate of iron, for example patients with haemoglobin levels below 10 g/dL. Importantly, the applicants have shown that a 90 mg dose can be safely administered; in addition in the event of overdose the risk of serious and potentially fatal, toxicity is reduced; making this treatment regime a realistic option in severely iron deficient patients.

The ST10 preparation is formulated as a 30 mg capsule or tablet and comprises:
231.5 mg ST10
91.5 mg lactose monohydrate
3.0 mg sodium lauryl sulphate
9.0 mg crospovidone
0.6 mg colloidal silicon dioxide
3.0 mg magnesium stearate In another embodiment the ST10 preparation is formulated as a 30 mg capsule or tablet and comprises:
231.5 mg ST10
80-110 mg lactose monohydrate
3.0 mg sodium lauryl sulphate
9.0 mg crospovidone
0.6 mg colloidal silicon dioxide
3.0 mg magnesium stearate The percentage of ST10 may be at least 60% of the combined weight of ST10 and excipients. ST10 may be administered once daily as a single 60 mg dose when the percentage of ST10 is at least 60% of the combined weight of ST10 and excipients.

The ST10 30 mg preparation may be formulated in a size 1 capsule.

The ST10 preparation may comprise varying amounts of other excipients for example lactose monohydrate, sodium lauryl sulphate, crospovidone, colloidal silicon dioxide, colloidal silicon dioxide and magnesium stearate.

The ST10 preparation may be comprised within a capsule or tablet and mixed with a pharmaceutically acceptable carrier for example suitable diluents, excipients or carriers selected with regard to oral administration. ST10 may be combined with an oral, non-toxic, inert carrier such as lactose, gelatin, agar, starch, sucrose, glucose, dicalcium phosphate, calcium sulfate, mannitol, sorbitol and microcrystalline cellulose. Suitable binders include starch, gelatin, natural sugars such as glucose or beta-lactose, corn starch, natural and synthetic gums such as acacia, tragacanth, or sodium alginate, povidone, carboxymethylcellulose, polyethylene glycol and waxes. Lubricants used in these dosage forms may include sodium oleate, sodium stearate, sodium benzoate, sodium acetate, sodium chloride, stearic acid, sodium stearyl fumarate, and talc. Disintegrators include, without limitation, starch, methyl cellulose, agar, bentonite, xanthan gum, croscarmellose sodium, and sodium starch glycolate.

In one embodiment the ST10 dose is administered orally. The ST10 dose may be administered as a solid dosage form or as a liquid formulation. An example of a suitable liquid formulation is provided in GB1404390.5.

Certain advantageous effects associated with ST10 treatment have been previously observed (GB1400171.3), for example the absence of blackened stools, which is a recognised side effect of ferrous iron treatment and is caused by excess iron in the gut and is an inherent feature of ferrous therapy due to the high doses of iron required. This observation of absence of blackened stools provides a significant advantage in terms of monitoring disease signs, particularly for patients who are suffering from IBD; gastrointestinal telangiectasia, oesophageal varices, or other vascular or coagulation abnormalities and have gastrointestinal bleeding since it allows clinicians to differentiate between bleeding (which causes blackened stools or melena) due to aforementioned conditions and excess iron in the gastrointestinal tract from the ferrous iron treatment. Therefore ST10 treatment is amenable to ongoing long term or maintenance treatment since it allows clinicians to associate blackened stools solely with the disease related events.

Furthermore it is appreciated that ST10 provides iron through the normal physiological route as it is swallowed and absorbed across the gut wall. Iron absorbed through ST10 is therefore under normal physiological control and absorption is down-regulated in subjects who have normal levels of iron through fewer iron transporting proteins being available at the enterocyte luminal surface. In this way, unlike conventional ferrous treatments, overload and toxicity of iron is not a significant risk with ST10 therapy. This low risk of iron overload provides another advantage for long term maintenance treatment using ST10 and provides another safety advantage in the event of an overdose. Iron treatments are commonly prescribed to women of childbearing age and there exists a risk to paediatric safety in the event of an overdose. The risk is significantly reduced for ST10 because the levels of elemental iron are much lower in comparison to ferrous products which if overdosed in children can result in death due to liver failure and ST10's iron uptake is controlled at the physiological level.

A 40 mg to 90 mg ST10 dose may be administered for any period until iron levels have increased to normal levels. For example a ST10 dose may be administered from a period of up to 16 weeks, but can be administered for as long as needed.

A 40 mg to 90 mg ST10 preparation may be administered indefinitely as a maintenance dose.

The ST10 doses described herein are amenable to combination therapies. For example it is known to combine iron supplements with hormonal contraception tablets to treat anaemia in child bearing women who suffer from menorrhagia. Such combinations carry an increased risk of ineffectiveness when combined with ferrous iron since the gastrointestinal side effects could lead to non-compliance and increased risk of pregnancy. ST10 may be safely combined with hormone contraceptive tablets since the observed side effects seen for ferrous iron are not observed.

The ST10 doses described herein may be administered at the same time as antacid treatment, for example compounds containing calcium, magnesium, and proton pump inhibitors (PPIs). ST10 doses may also be administered in diseases or situations that result in reduced or lack of gastric acid production for example after gastrectomy, in old age or atrophic or autoimmune gastritis. In contrast ferrous tablets should not be taken with stomach pH raising medications as this reduces the bioavailability of iron from ferrous products.

The ST10 doses described herein are useful in the treatment of iron deficiency with or without anaemia. For the avoidance of doubt, iron deficiency with or without anaemia relates to all diseases and conditions associated with iron deficiency and for which treatment with iron would be therapeutically beneficial. Such diseases are those which are recognised as having iron deficiency as a complication or symptom. Iron deficiency is also referred to as sideropenia or hypoferremia and results from a prolonged period of inadequate iron intake; this medical state is called Latent Iron deficiency (LID) or Iron-deficient Erythropoiesis (IDE).

Symptoms of iron deficiency can be apparent before iron deficiency anaemia and include but are not limited to fatigue, hair loss, twitches, irritability, dizziness, brittle or grooved nails, appetite disorders such as pica and pagophagia, impaired immune function, chronic heart failure, growth, behaviour and learning in children, cognition in the elderly and Plummer-Vinson syndrome (PVS).

Conditions associated with iron deficiency anaemia include, but are not limited to chronic kidney disease (CKD), Systemic Lupus (SLE), rheumatoid arthritis, haematological cancers (e.g. Hodgkin's disease), chronic bacterial infection (e.g. osteomyelitis), viral hepatitis, HIV, AIDS, diseases of the gastrointestinal tract for example inflammatory bowel diseases (IBD) such as Crohn's disease and ulcerative colitis.

The study described herein reports the treatment of subjects suffering from iron deficiency with or without anaemia having active inflammatory disease or acute chronic inflammation. In previous studies reported, such patients were excluded because the production of cytokines in states of chronic inflammation, such as IL-10, lipopolysaccharide, TNF-alpha and hepcidin act via multiple mechanisms to increase the uptake and storage of iron in the reticuloendothelial system, and reduce the uptake of iron from the gut.

It is appreciated that inflammatory bowel diseases (IBD) such as Crohn's disease and ulcerative colitis may be in the active state (or flare) as described above, or in remission.

In one embodiment the 40 mg to 90 mg ST10 dose described herein is useful in the treatment or prevention of iron deficiency with or without anaemia, wherein the iron deficiency is a result of, or associated with active inflammatory disease or acute chronic inflammation.

Therefore, there is provided ST10 for use in the treatment or prevention of active inflammatory disease or acute chronic inflammation wherein ST10 is administered orally as a single 40 mg to 90 mg dose twice daily.

In another example there is provided ST10 for use in the treatment or prevention of active inflammatory disease or acute chronic inflammation wherein ST10 is administered orally as a single 60 mg dose twice daily.

In a further example there is provided ST10 for use in the treatment or prevention of active inflammatory disease or acute chronic inflammation wherein ST10 is administered orally as a single 60 mg to 90 mg dose once daily.

In another embodiment the ST10 doses described herein are useful in the treatment of chronic kidney disease (CKD). One of the recognised symptoms of this condition is iron deficiency with and without anaemia and so the ST10 dosages described herein provide a safe, effective and manageable treatment for subjects who are already taking one or more other medications.

In another aspect the invention relates to a method of treating a subject suffering from iron deficiency with or without anaemia the method comprising administering orally to the subject a ST10 dose described herein twice daily.

In one embodiment there is provided a method of treating a subject suffering from iron deficiency with or without anaemia the method comprising administering orally to the subject a 65 mg to 90 mg ST10 dose described herein once daily.

EXAMPLES

These studies were primarily pharmacokinetic and conducted in subjects with iron deficiency having active inflammatory disease or acute chronic inflammation. An open-label, randomised, single and repeat dose parallel group Phase I pharmacokinetic study was carried out to evaluate the effect of single and repeated twice daily (bid) oral doses of ST10 at 30 mg, 60 mg and 90 mg for 8 days.

24 subjects with iron deficiency (with or without anaemia) were randomly allocated to one of the three ST10 dose groups as follows:

Group 1: 9 subjects received ST10, 30 mg twice daily for 7 days (days 1-7) plus a final 30 mg dose on the morning of day 8.

Group 2: 8 subjects received ST10, 60 mg twice daily for 7 days (days 1-7) plus a final 60 mg dose on the morning of day 8.

Group 3: 7 subjects received ST10, 90 mg twice daily for 7 days (days 1-7) plus a final 90 mg dose on the morning of day 8.

On day 1, following fasting for at least 1.5-2 hours beforehand, ST10 was administered (30 mg, 60 mg or 90 mg) and blood samples collected over the following 6 h for analysis. 60 mg was administered as two 30 mg capsules and 90 mg was administered as three 30 mg capsules, both as a single dose. Subjects continued dosing with ST10 on the evening of day 1 then every morning and evening for the next 6 days (Days 2 to 7).

On day 8 following fasting for at least 1.5-2 hours beforehand the last dosing of ST10 was administered (30 mg, 60 mg or 90 mg) and blood samples collected over the following 6 h for analysis.

On Days 1 and 8 blood samples were collected predose (0 h=time of ST10 dose) and at 5 minutes(for NTBI only), 15 minutes, 30 minutes, 45 minutes, and 1, 1.5, 2, 3, 4 and 6 h postdose.

Serum concentrations of transferrin, total iron binding capacity (TIBC), ferritin and soluble transferrin receptor; and reticulocyte haemoglobin concentrations (CHr) in whole blood were measured by central laboratories using appropriately validated methods.

These studies used transferrin saturation and total serum iron as measurements of iron uptake from the gut into the transport mechanisms. In addition serum ferritin was used as a measure of iron storage status at the end of the dosing period; all of these measurements are standard and well recognised.

One subject in the 60 mg dose group prematurely withdrew from the study on Day 7, so full profiles of all serum iron parameters were available in the 30 mg dose group for 9 subjects (days 1 and 8), in the 60 mg dose group 8 subjects on day 1 and for 7 subjects on day 8, and in the 90 mg dose group for 7 subjects (days 1 and 8).

RESULTS

Total Iron Serum Concentration and Total Iron Binding Capacity.

Figure 1:
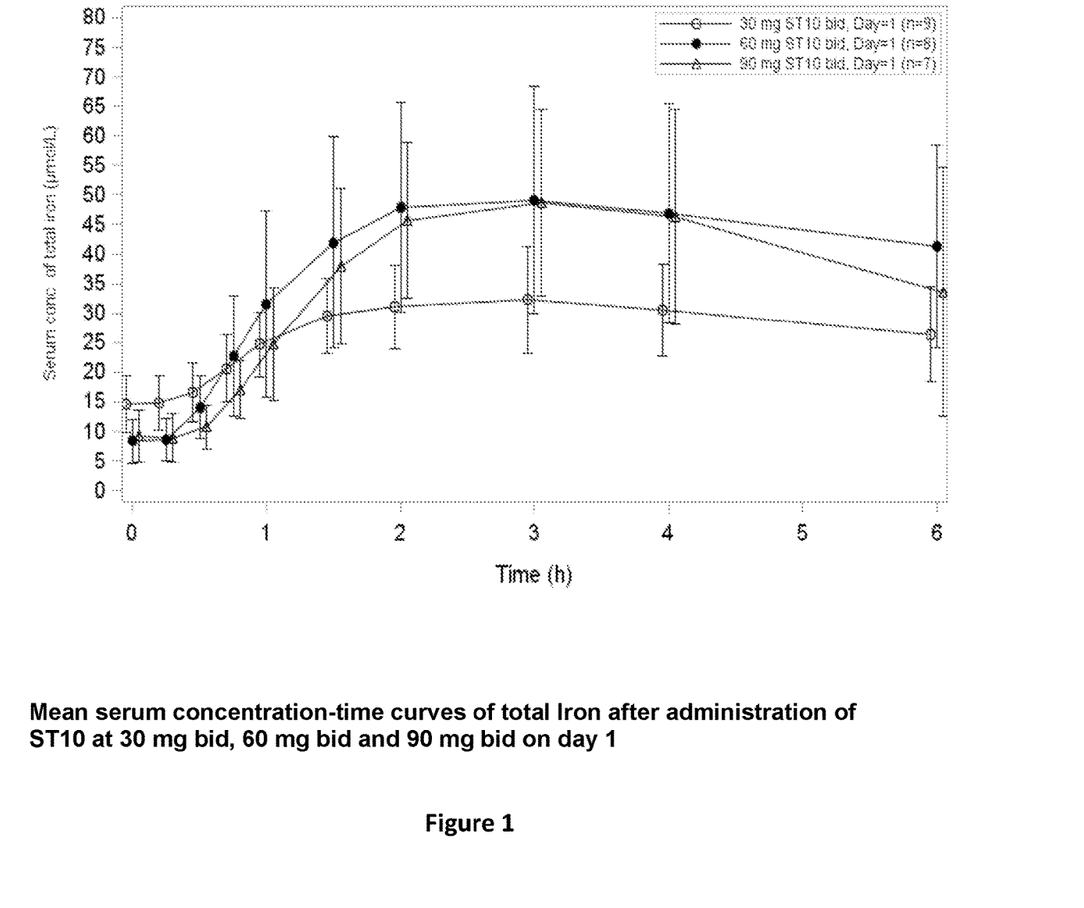
FIG. 1 shows a graph of mean serum concentration of total iron over 6 hours after administration of ST10 at doses of 30 mg bid, 60 mg bid, 90 mg bid on day 1.
Figure 2:
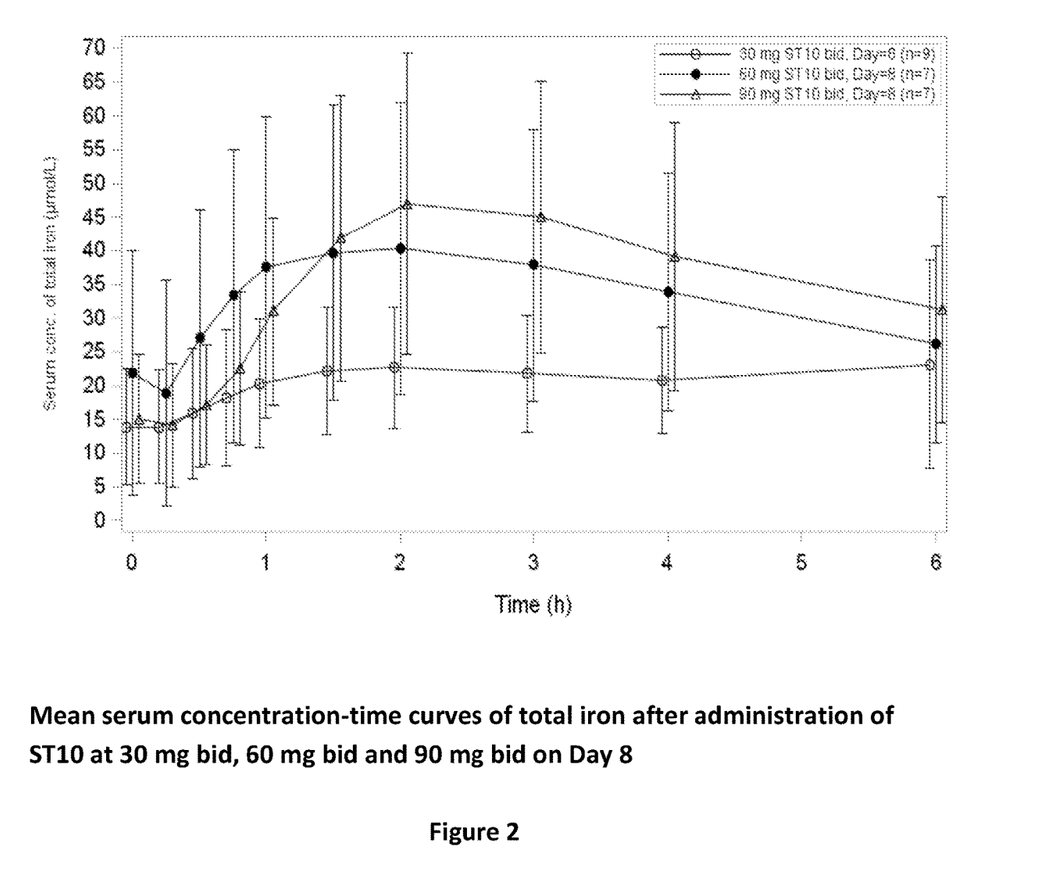
FIG. 2 shows a graph of mean serum concentration of total iron over 6 hours after administration of ST10 at doses of 30 mg bid, 60 mg bid, 90 mg bid on day 8.

Maximum serum concentrations of total iron were reached between 2 and 3 h postdose. Initially a slight decline in serum total iron concentrations was observed, followed by an increase to on average 32.3, 49.1 and 48.7 µmol/L on Day 1 for the 30 mg, 60 mg and 90 mg dose groups, respectively. Serum total iron concentrations gradually declined after reaching $t_{max}$ (time to reach the maximal observed analyte concentration) and mean serum concentrations were 11.8, 33.0 and 24.3 µmol/L above baseline at 6 h postdose on Day 1 for the 30 mg, 60 mg and 90 mg dose groups, respectively. Comparable serum concentrations were measured on Day 8. (FIGS. 1 and 2)

Total iron binding capacity remained fairly constant over time and between dose groups with a mean concentration of approximately 70 µmol/L and individual values ranged between 47 and 101 µmol/L.

The results indicate that doses above 30 mg and up to 90 mg are well tolerated and allow for a higher level of iron absorption than observed for the standard 30 mg dose.

Transferrin and Transferrin Saturation (TSAT)

Transferrin binds iron reversibly in the plasma and transports it into the cell via binding to the transferrin receptor. An increased plasma transferrin level is an indicator of iron deficiency anaemia.

Figure 3:
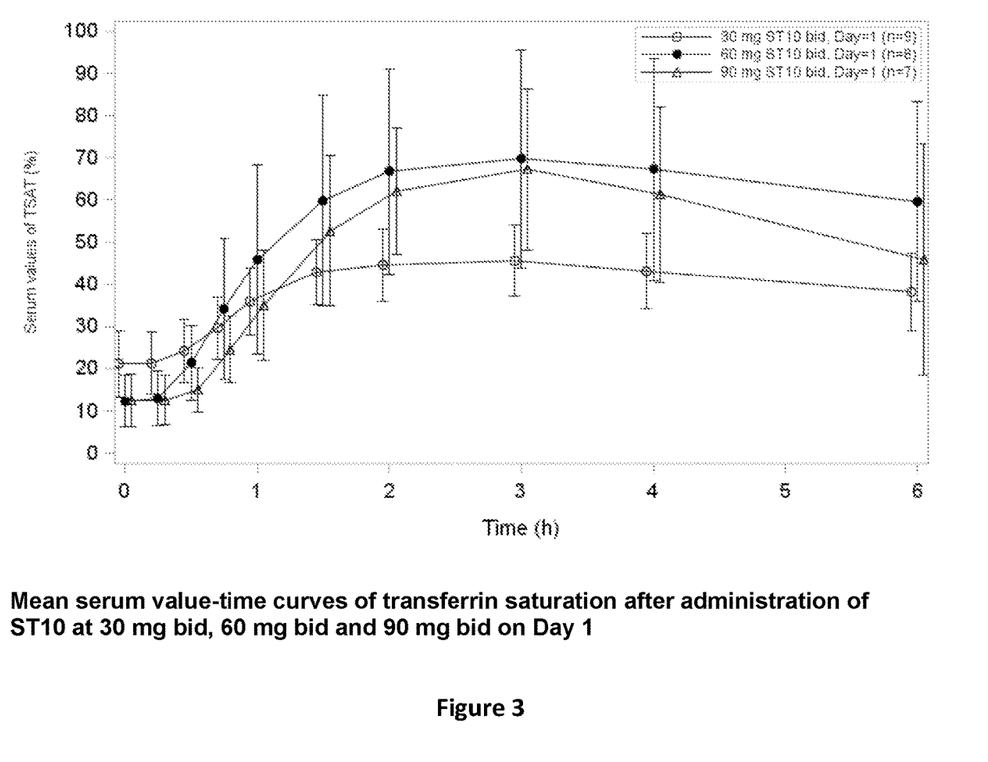
FIG. 3 shows a graph of mean serum values over 6 hours of transferrin saturation after administration of ST10 at doses of 30 mg bid, 60 mg bid, 90 mg bid on day 1.
Figure 4:
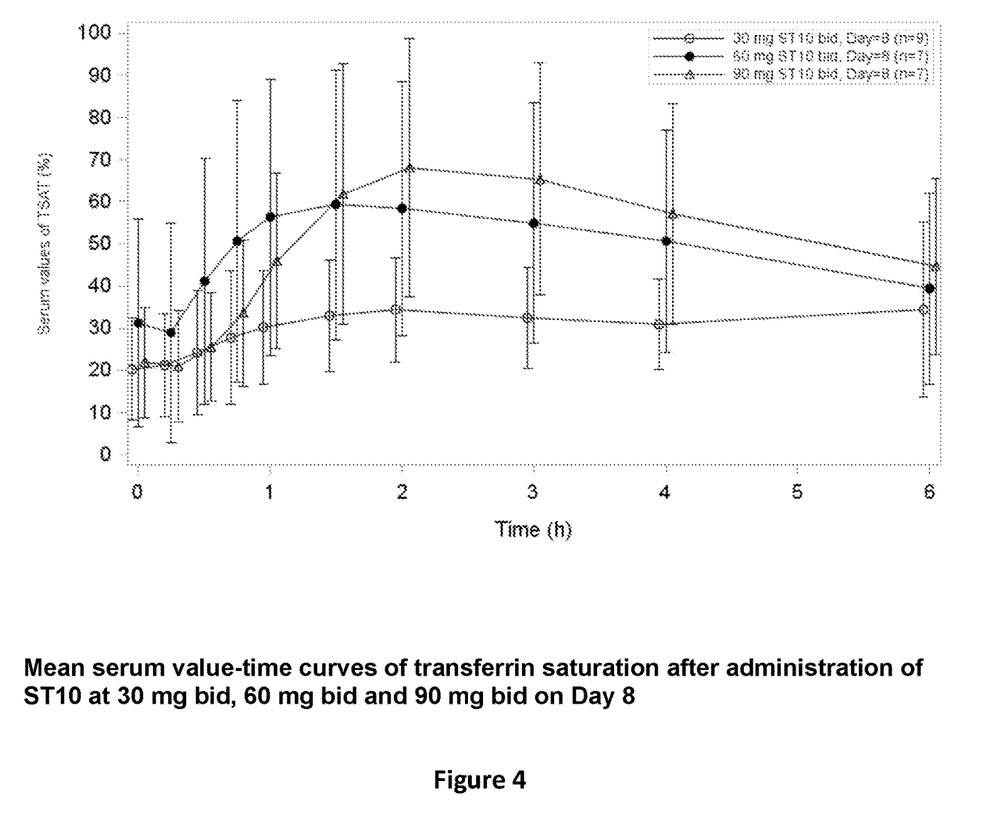
FIG. 4 shows a graph of mean serum values over 6 hours of transferrin saturation after administration of ST10 at doses of 30 mg bid, 60 mg bid, 90 mg bid on day 8.

Maximum serum values of TSAT were reached between 2 and 3 h post-dose. Transferrin saturation values gradually increased up to an average value of 45.6, 69.8 and 67.3% on Day 1 for the 30 mg, 60 mg and 90 mg dose groups, respectively. Transferrin saturation gradually declined after reaching $t_{max}$ (time to reach the maximal observed analyte concentration) and serum values were 17.0, 47.3 and 33.3% above baseline at 6 h postdose on Day 1 for the 30 mg, 60 mg and 90 mg dose groups, respectively (FIG. 3). Similar TSAT serum values were measured on Day 8 (FIG. 4).

Figure 5:
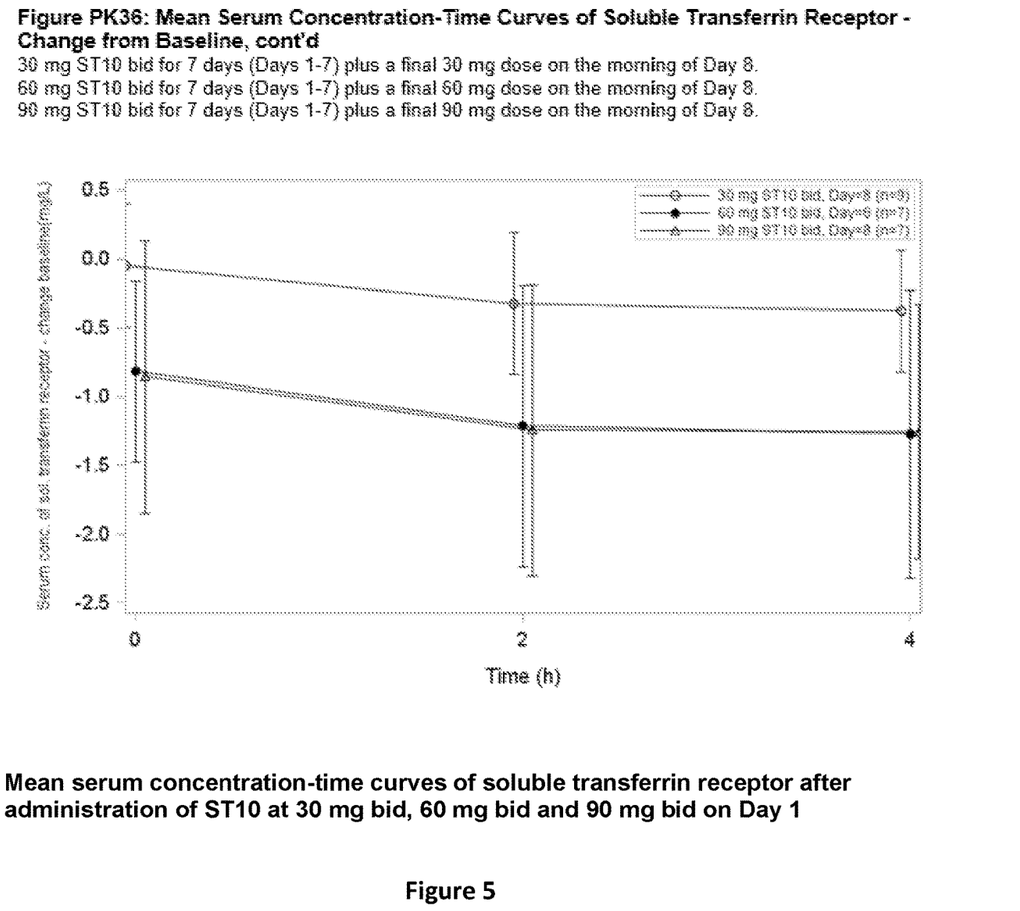
FIG. 5 shows a graph of serum concentration of soluble transferrin receptor over 4 hours after administration of ST10 at doses of 30 mg bid, 60 mg bid, 90 mg bid on days 1-7 and a single dose of 30 mg bid, 60 mg bid, 90 mg on day 8.

Soluble transferrin receptor remained fairly constant over time and between dose groups, with a mean concentration of approximately 4 mg/L and individual values ranged between 1.8 mg/L and 9.3 mg/L. Soluble transferrin receptor concentration decreases in response to iron treatment. FIG. 5 shows no difference between the 60 mg and 90 mg dose, however in comparison the concentration of sTFr is significantly higher for the 30 mg dose, supporting the finding that doses above 30 mg and up to 90 mg are well tolerated and effective.

The results show that the rise in transferrin saturation after a single dose is at least as large for twice the 60 mg dose, compared to 30 mg (FIGS. 3 and 4) suggesting that a maintenance dose of 30 mg twice daily can be given as a single 60 mg dose thereby improving adherence and clinical outcome.

Ferritin Concentrations

Ferritin is an intracellular protein that stores iron in a soluble and non-toxic form and small amounts are secreted into the serum where it functions as an iron carrier. Hence plasma ferritin is an indirect marker for the total amount of iron stored in the body and can be used to detect iron deficiency. High ferritin levels indicate the presence of excess iron and thus a correction in iron deficiency.

Figure 6:
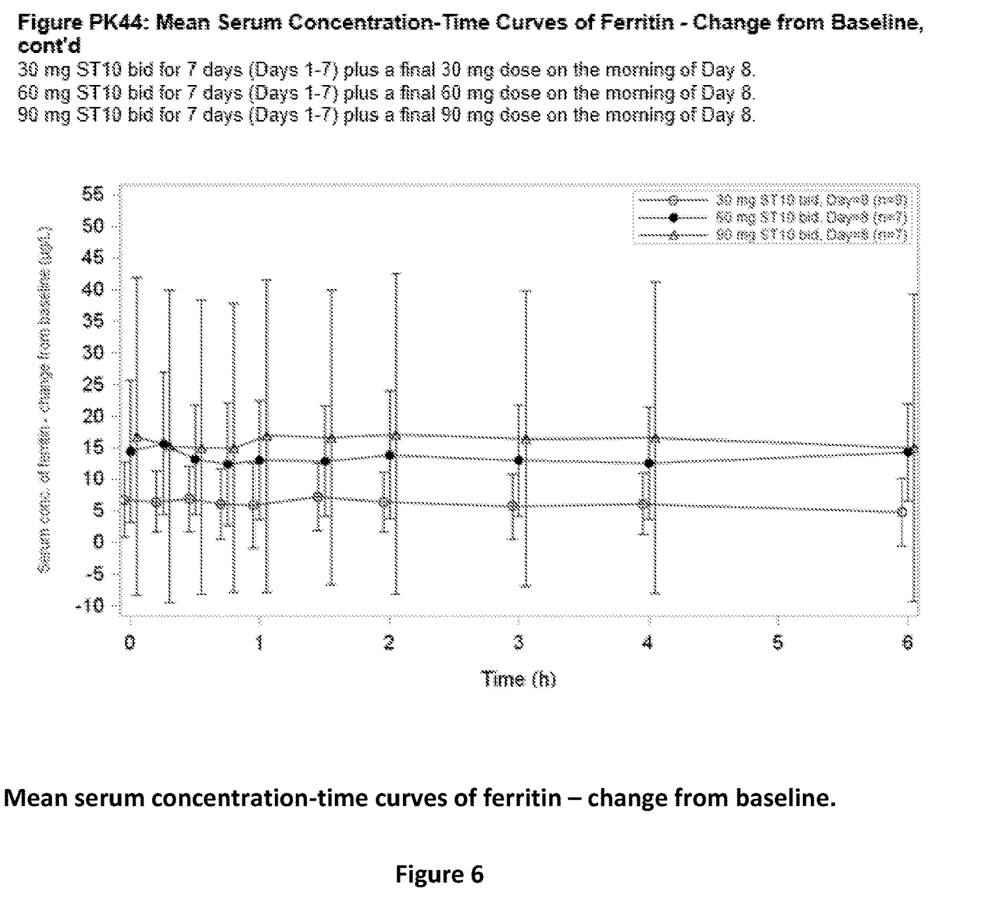
FIG. 6 shows a graph of mean serum concentration of ferritin over 6 hours after administration of ST10 at 30 mg bid, 60 mg bid, 90 mg bid on days 1-7 and a single dose of 30 mg bid, 60 mg bid, 90 mg on day 8.

Mean ferritin concentrations remained fairly constant over the individual concentration time profiles, with higher ferritin serum concentrations on day 8 compared to day 1. Mean serum ferritin values for the 30 mg, 60 mg and 90 mg dose groups were around 15 µg/L, 10 µg/L and 13 µg/L on day 1 and 22 µg/L, 22 µg/L and 32 µg/L on day 8, respectively. On day 8 the results show that there were higher concentrations of ferritin in the serum for the 60 mg and 90 mg dose in comparison to the 30 mg dose suggesting that the higher doses are more effective at correction iron deficiency (FIG. 6).

Reticulocyte Haemoglobin (Hb)

This study measured reticulocyte haemoglobin. Reticulocytes are immature red blood cells, formed in the bone marrow but also found in the circulating blood. They represent less than 5% of the red blood cell mass, but provide an early indicator of change in total haemoglobin Low numbers of reticulocytes or immature red blood cells are a marker for the presence of anaemia and so measurement of the levels of haemoglobin allows progression of treatment for anaemia to be monitored.

TABLE 1

| Dose | Baseline | Day 8 | Mean change |
| --- | --- | --- | --- |
| 30 mg bid | 33.6 | 34.6 | 0.9 |
| 60 mg bid | 31.0 | 34.1 | 3.3 |
| 90 mg bid | 30.8 | 33.9 | 3.0 |

In this study we saw that all doses of ST10 gave an increase in reticulocyte haemoglobin (Table 1). However, importantly 60 mg twice a day gave a greater reticulocyte haemoglobin rise compared to 30 mg twice a day; therefore in a longer treatment period and in a larger study we could reasonably expect 60 mg twice a day to produce an improved clinical outcome with regard to anaemia correction. This suggests that a dose of ST10 above 30 mg has an improved clinical benefit in terms of correcting iron deficiency.

The rate of improvement of Haemoglobin (Hb) content in reticulocytes seen over 8 days is evidence of the incorporation of iron into normal physiological functions and therefore translates to a clinical benefit associated with the dose administered.

REFERENCES

1. Bergamaschi G. et al Prevalence and pathogenesis of anaemia in inflammatory bowel disease. Haematological 2010; 95:199-205
2. Wilson A. et al. Prevalence and outcomes of anaemia in inflammatory bowel disease. A systematic review of the literature. Am J Med 2004; 116(7A):44S-49S.
3. Dudkowiak R. et al. Hepcidin and its role in inflammatory bowel disease. Adv Clin Exp Med. 2013; July-August; 22(4):585-91.
4. Kawai M, Summimoto S, Kasajima Y, Hamamoto T. A case of ulcerative colitis induced by oral ferrous sulphate. Acta PaediatrJpn 1992; August; 34(4):476-8.
5. British National Formulary, Nutrition and Blood. BMJ Publishing Group and RPS Publishing London 2006; 51:463-4.
6. Rimon E, Kagansky M et al, Are we giving too much iron? Low dose iron therapy is effective in octogenarians. Am J Med 2005; 118(10):1142-7.
7. Makrides M, Crowther C A, Gibson R A. et al, Efficacy and tolerability of low-dose iron supplementation during pregnancy; a randomised controlled trial. Am J Clin Nutr 2003; 78(1):145-53.
8. Kerr DNS. et al. Gastrointestinal tolerance to iron. Lancet 1958; ii: 489-92.
9. Brise H. et al. Absorbability of different iron compounds. Acta Med Scand. 1962; 171 (Suppl. 376): 23-37.
10. Slivka A. et al Hydroxyl radicals and toxicity or oral iron. Biochem Biopharmacol 1986; 35: 553-6
11. Gasche, C. et al. Correcting iron deficiency anaemia in IBD: A pivotal phase 3 study of a novel oral ferric iron. AEGIS Study ECCO Late Breaker 2014 (Abstract).
12. Kelsey, S. M., et al. Absorption of low and therapeutic doses of ferric maltol, a novel ferric iron compound, in iron deficient subjects using a single dose iron absorption test. J. Clinical Pharmacy and Therapeutics.1991; 16, 117-122.
13. Harvey, R. S. J., et al. Ferric trimaltol corrects iron deficiency anaemia in patients intolerant of iron. Aliment Pharmacol Ther 1998; 12: 845-848.

The invention claimed is:

1. A method of treating iron deficiency in a subject with or without anaemia having inflammatory disease or acute inflammation, comprising orally administering to the subject a 40 mg to 90 mg dose or a 65 mg to 90 mg dose of ferric trimaltol, wherein 40 mg to 90 mg or 65 mg to 90 mg refers to the amount of elemental iron in the dose; and wherein the 40 mg to 90 mg dose is administered twice daily to achieve a total daily dose of 80 mg to 180 mg elemental iron, or wherein the 65-90 mg dose is administered once daily; and wherein the inflammatory disease or acute inflammation is selected from chronic kidney disease (CKD), Systemic Lupus (SLE), rheumatoid arthritis, a haematological cancer, a chronic bacterial infection, viral hepatitis, HIV, AIDS and a disease of the gastrointestinal tract.

2. The method according to claim 1 wherein the dose is between 60 mg to 90 mg, wherein the dose is administered twice daily to achieve a total daily dose of 120 mg to 180 mg elemental iron.

3. The method according to claim 1 wherein the dose is between 65 mg to 90 mg, wherein the dose is administered once daily.

4. The method according to claim 1 wherein the dose is 90 mg, wherein the dose is administered twice daily to achieve a total daily dose of 180 mg elemental iron.

5. The method according to claim 1 wherein the dose is 60 mg, wherein the dose is administered twice daily to achieve a total daily dose of 120 mg elemental iron.

6. The method according to claim 1 wherein the dose is administered on two separate occasions during the waking hours.

7. The method according to claim 6 wherein the dose is administered on an empty stomach.

8. The method according to claim 3 wherein the 90 mg dose is administered orally once daily.

9. The method according to claim 1 wherein the dose is administered for up to a 16 week period.

10. The method according to claim 1 wherein the dose is administered indefinitely as a maintenance dose.

11. The method according to claim 10 wherein the dose is administered orally every two, three, four, five, six or seven days.

12. The method according to claim 1 wherein iron deficiency is iron deficiency with anaemia.

13. The method according to claim 1 wherein the iron deficiency is caused by a disease of the gastrointestinal tract selected from Crohn's disease and ulcerative colitis.

14. The method of claim 1, wherein iron deficiency is caused by Hodgkin's disease, osteomyelitis or inflammatory bowel disease.

15. A method of treating iron deficiency in a subject with or without anaemia having inflammatory disease or acute chronic inflammation, comprising orally administering to the subject a 40 mg to 90 mg dose or a 65 mg to 90 mg dose of ferric trimaltol, wherein 40 mg to 90 mg or 65 mg to 90 mg refers to the amount of elemental iron in the dose; and wherein the 40 mg to 90 mg dose is administered twice daily to achieve a total daily dose of 80 mg to 180 mg elemental iron, or wherein the 65-90 mg dose is administered once daily.

16. The method according to claim 15 wherein the dose is between 60 mg to 90 mg, wherein the dose is administered twice daily to achieve a total daily dose of 120 mg to 180 mg elemental iron.

17. The method according to claim 15 wherein the dose is between 65 mg to 90 mg, wherein the dose is administered once daily.

18. The method according to claim 15 wherein the dose is 90 mg, wherein the dose is administered twice daily to achieve a total daily dose of 180 mg elemental iron.

19. The method according to claim 15 wherein the dose is 60 mg, wherein the dose is administered twice daily to achieve a total daily dose of 120 mg elemental iron.

20. The method according to claim 15 wherein the dose is administered on two separate occasions during the waking hours.

21. The method according to claim 20 wherein the dose is administered on an empty stomach.

22. The method according to claim 17 wherein the 90 mg dose is administered orally once daily.

23. The method according to claim 15 wherein the dose is administered for up to a 16 week period.

24. The method according to claim 15 wherein the dose is administered indefinitely as a maintenance dose.

25. The method according to claim 24 wherein the dose is administered orally every two, three, four, five, six or seven days.

* * * * *

UNITED STATES PATENT AND TRADEMARK OFFICE
CERTIFICATE OF CORRECTION

| | |
|---|---|
| PATENT NO. | : 10,786,514 B2 |
| APPLICATION NO. | : 15/520753 |
| DATED | : September 29, 2020 |
| INVENTOR(S) | : Nicholas Mallard et al. |

It is certified that error appears in the above-identified patent and that said Letters Patent is hereby corrected as shown below:

On the Title Page

At item (30), delete "Oct. 21, 2015" and replace with --Oct. 21, 2014--

Signed and Sealed this
Twentieth Day of September, 2022

Katherine Kelly Vidal
*Director of the United States Patent and Trademark Office*